US006524592B2

(12) United States Patent
Buchta et al.

(10) Patent No.: US 6,524,592 B2
(45) Date of Patent: Feb. 25, 2003

(54) VETERINARY VACCINES

(75) Inventors: Richard Buchta, Westleigh (AU); Christopher Leigh Schwartzkoff, Turramurra (AU); Philip Ralph Lehrbach, Wahroonga (AU)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/509,961

(22) PCT Filed: Oct. 16, 1998

(86) PCT No.: PCT/AU98/00865
§ 371 (c)(1),
(2), (4) Date: May 23, 2000

(87) PCT Pub. No.: WO99/20305
PCT Pub. Date: Apr. 29, 1999

(65) Prior Publication Data
US 2002/0098204 A1 Jul. 25, 2002

(30) Foreign Application Priority Data
Oct. 17, 1997  (AU) .............................................. 9722035

(51) Int. Cl.$^7$ ............................................. A61K 45/00
(52) U.S. Cl. ............................... 424/278.1; 424/234.1; 424/184.1
(58) Field of Search ............................... 424/92, 234.1, 424/278.1, 184.1

(56) References Cited

U.S. PATENT DOCUMENTS

| | | | | |
|---|---|---|---|---|
| 3,869,546 A | * | 3/1975 | Lund ........................... | 424/88 |
| 4,140,763 A | * | 2/1979 | Bachrach et al. ............. | 424/89 |
| 4,292,307 A | * | 9/1981 | Zemlyakova ................. | 424/92 |
| 4,748,019 A | * | 5/1988 | Lysons ......................... | 424/92 |
| 4,795,635 A | * | 1/1989 | Peleg et al. .................... | 424/89 |
| 4,806,350 A | * | 2/1989 | Gerber ......................... | 424/88 |
| 5,422,109 A | * | 6/1995 | Brancq et al. ........... | 424/184.1 |
| 5,424,067 A | | 6/1995 | Brancq et al. | |
| 5,573,767 A | * | 11/1996 | Dufour et al. ......... | 424/195.11 |
| 5,622,649 A | * | 4/1997 | Hunter et al. ................ | 252/309 |
| 5,874,486 A | * | 2/1999 | Bastioli et al. ............. | 523/128 |
| 5,885,590 A | * | 3/1999 | Hunter et al. ............ | 424/280.1 |
| 5,989,566 A | * | 11/1999 | Cobb et al. ............. | 424/278.1 |
| 6,015,832 A | * | 1/2000 | Baker, Jr. et al. ........... | 514/546 |
| 6,083,512 A | * | 7/2000 | Roberts .................... | 424/247.1 |
| 6,342,234 B1 | * | 1/2002 | Ganne ..................... | 424/278.1 |

FOREIGN PATENT DOCUMENTS

| | | |
|---|---|---|
| GB | 1128325 | 9/1968 |
| WO | WO97/46204 | 12/1997 |

OTHER PUBLICATIONS

Dodson, LF, Australian veterinary journal, Dec. 1978, vol. 54(12), pp. 598–599 (abstract only).*
Reed, GA et al, Australian veterinary journal, Aug. 1977, vol. 53(8), p. 393 (abstract only).*
Campbell, Ailsa M., Laboratory Techniques in Biochemistry and Molecular Biology, vol. 23, Chapter No. 1, pp. 1–49, Elsevier publishers, 1991.*
Schwartzkoff, CL et al, Australian veterinary journal, Sep. 1996, vol. 74(3), pp. 225–227 (abstract only).*
Muneer, R et al, Revue scientifique et technique, Sep. 1994, vol. 13(3), pp. 837–843 (abstract only).*
Jansen, et al., The Antibody Response of Cattle to Clostridium Botulinum Types C and D Toxoids, Onderstepoort J. vet Res. 43 (4), 165–174 (1976).
Thomson, et al., Experimental Clostridial Oil Emulsion Vaccines, Bull. Off. Int. Epiz., 67 (11–12), 1569–1581, (1967).
Thomson, et al., The Immunogenicity of a Multicomponent Clostridial Oil Emulsion Vaccine in Sheep, 85, 81–85, (1969).

* cited by examiner

*Primary Examiner*—Lynette R. F. Smith
*Assistant Examiner*—Ginny Allen Portner
(74) *Attorney, Agent, or Firm*—Adley F. Mandel; John F. Levis

(57) ABSTRACT

The invention relates to vaccines which are suitable for the prevention of clostridial diseases of sheep (and lambs), providing an effective immunity for up to a year or more following a single injection or dose.

15 Claims, No Drawings

VETERINARY VACCINES

The present invention relates to novel vaccine compositions for parenteral administration, methods for their use and to processes for their preparation. Bacterial and viral diseases of sheep, such as Clostridial diseases, cause considerable economic damage in the agriculture industry. Vaccination is therefore a very important means of controlling these diseases.

Many currently available vaccines are comprised of killed antigens, whether inactivated bacterial cells, viral particles or cellular components, absorbed onto alkali earth metal salts (i.e. aluminium phosphate or aluminium hydroxide) or as water in oil emulsions. For these vaccines it is recommended that naive animals (i.e. animals which have not been previously vaccinated) are treated in a two stage dose regime consisting of an initial dose and a second booster dose several weeks later. The action of the booster dose raises the antibody titre to a level that may sustain protection from a disease causing challenge organism for an extended period. Animals undergoing this vaccination program are usually mustered each year for revaccination. Clearly such initial two-dose administration is time consuming and expensive and is therefore undesirable.

The aluminium based vaccines have been found to have relatively short duration of protection while water-in-oil emulsion vaccines have a longer duration of protection but have been found to be unsuitable for use because they cause unacceptable lesions at the injection sites of the animals ('Experimental Clostridial Oil Emulsion Vaccines' Thomson R O. and Batty I., Bull. Off. int Epiz. 1967 67 (11–12) 1569–1581; 'The Immunogenicity of a multicomponent Clostridial Oil Emulsion Vaccine in sheep' Thomson et al The Veterinary Record, Jul. 26, 1969). In 1976 Jansen et al. reported the immune response of *Cl. botulinum* C and D toxoids in a water-in-oil emulsion vaccine and noted that the two-stage aluminium based vaccine was not boosted by the second dose to the same extent as the water in oil compositions (Jansen, B C, Knoetze, P C & Visser, F; Onderstepoort J Vet Res, 43(4) 165–174 (1976)). However, the water in oil compositions gave an undesirable granulomatous swelling resulting from subcutaneous injection of the vaccine in a large percentage of animals which is a severe disadvantage for the vaccine's commercial use.

WO91/00106 discloses multi-phase emulsions suitable for administering active substances or antigens by injection of the water in oil in water type. These emulsions are produced from pharmaceutically acceptable emulsifiers which when dissolved in an injectable oil, form a homogeneous clear phase and have inversion points approaching the temperature of human or animal bodies. The oils contained in the emulsions include mineral, vegetable or animal oils, and synthetic hydrocarbons. It was observed that these vaccines were well tolerated in pigs and did not cause any local reactions, abscesses or necroses. However, no data were provided regarding the level and duration of the immune responses.

The applicants provide vaccines which are suitable for the prevention of clostridial diseases of sheep and in particular lambs, providing an effective immunity for up to a year or more following a single injection or dose. Therefore, the present invention addresses the problems associated with known vaccines, providing a level of effective immune response in sheep for the period of approximately one year or more following a single injection or dose of vaccine. The present invention also provides vaccines which provide an effective immunity against each of a number of diseases for up to a year or more following a single injection or dose of a multivalent vaccine. The selection of an adjuvant which enhances the antigenic response to clostridial antigens in sheep is thus a problem addressed by the invention. The selection of an adjuvant which enhances the antigenic response to each of a number of micro-organisms in sheep is a particular problem addressed by the invention.

Thus according to the present invention there is provided a sheep vaccine composition comprising:
a) an oily adjuvant acceptable for veterinary purposes comprising:
   i) a white mineral oil having a molecular weight of about 250 to 300 and
   ii) a mannitol oleate emulsifier and
b) an aqueous phase comprising one or more clostridial antigens.

When used herein the term "sheep" refers to lambs as well as developing and mature sheep. The vaccines of the invention are particularly useful in the vaccination of lambs.

The vaccine composition is an injectable emulsion of the water in oil type and preferably has a viscosity of about 200 mPas or less, more preferably about 100 mPas to about 150 mPas. The white mineral oil is preferably between about 50% and about 70% by weight of the emulsion more preferably between about 53% and about 63% by weight of the emulsion. The mannitol oleate emulsifier is preferably between about 2% and about 10% by volume of the emulsion more preferably between about 3% and about 7%.

The white mineral oil has a molecular weight of about 250 to 300, preferably about 270 to 290, more preferably about 280. The oil is preferably one which is liquid at 4° C. and has a viscosity lower than 100 mPas at 25° C. It preferably has a density at 20° C. of about 815 to 840 kg/m$^3$, more preferably about 817 to 837 kg/m$^3$. The dynamic viscosity of the oil at 25° C. is preferably about 5 to 15 mPas, more preferably about 6 to 13 mPas. The oil preferably has a kinematic viscosity at 40° C. of about 5 to 10 mm$^2$/s, more preferably about 7.5 mm$^2$/s. Preferred embodiments of the invention include the commercially available oil Marcol 52 which is supplied by ESSO.

The mannitol oleate emulsifier is preferably an anhydromannitol ether octadecanoate. Preferred emulsifiers have a viscosity at 25° C. of about 300 to 400cP, more preferably about 340 to about 360 cP, particularly preferred embodiments are those in which the emulsifier has a viscosity of about 350 cP. The emulsifier preferably has a specific gravity at 20° C. of about 0.8 to 1.0, more preferably of about 0.95 to about 0.99, particularly suitable are those with a specific gravity at 20° C. of about 0.97. Particularly preferred emulsifiers are those with a refractive index at 25° C. of about 1.4 to 1.5, more preferably of about 1.47 to 1.48, particularly those with a refractive index at 25° C. of about 1.4748 to 1.4758. Particularly preferred oils are the commercially availably ones Montanide 80, Montanide 103 and Montanide 888 supplied by SEPPIC SA, 75 Quai D-Orsay, 75007 Paris. Montanide 103 and Montanide 888 being more preferred and Montanide 888 being most preferred.

It will be apparent to a person of skill in the art that the proportion of oily adjuvant to aqueous phase included in the emulsion can be adjusted to optimise vaccines including particular antigens and for use in particular animals. It can also be modified to optimise vaccines for administration at a particular site.

The site of administration may also affect the efficacy and/or the site reactions caused by the vaccines. It will be apparent to a person of skill in the art that the site of administration can be selected so as to optimise the effects of vaccines including particular antigens and for use in particular animals. The vaccines exemplified herein were found to be efficacious regardless of site of administration, however site reactions from the exemplified vaccines were more numerous when they were administered at the brisket.

Clostridial antigens suitable for use in the compositions of the present invention include *Clostridium perfringens* type A, B, C and D, *Clostridium septicum, Clostridium tetani, Clostridium chauvoei, Clostridium novyi* type B, *Clostridium sordelli, Clostridium haemolyticum, Clostridium chauvoei* and *Clostridium botulinum* C and D. Suitable antigens include those which are useful in the treatment of diseases such as Lamb dysentery, Pulpy Kidney disease (enterotosemia), Malignant Oedema (blood poisoning), Tetanus, Blackleg disease and Black disease.

Antigens suitable for use in the present invention are any which provide a suitable immune response, e.g. toxoids or anacultures. Suitable antigens include *Clostridium perfringens* A, B, C and D toxoids; *Clostridium novyi* B toxoid; *Clostridium chauvoei* anaculture; *Clostridium septicum* toxoid, *Clostridium tetani* toxoid and *Clostridium sordelli* toxoid.

The vaccine is preferably a multi-valent vaccine, i.e. a vaccine providing protection against a number of different clostridial diseases by incorporating a number of different clostridial antigens e.g. the vaccine may contain any number of antigens selected from the list provided above. It is particularly useful to provide a multivalent vaccine, i.e. one which provide adequate immune response to a number of pathogens to increase the protection provided by the vaccine. It is particularly difficult to provide multivalent vaccines because it is necessary to provide a vaccine which induces an adequate antigenic response to all the microorganisms of interest. Thus the threshold antibody responses are described in compendial standards (e.g. Australian Therapeutic Goods order No. 30; British Pharmacopoeia; European Pharmacopoeia and United States Code of Federal regulation). Where compendial standards do not exist (e.g. for *Corynebacterium pseudotuberculosis*) recognised thresholds based on protection from challenge are accepted.

Preferred embodiments of the invention are vaccines comprising at least two types of clostridial antigen, each one being active against any one of the following: *Clostridium perfringens; Clostridium novyi, Clostridium chauvoei; Clostridium septicum* and *Clostridium tetani*. Particularly preferred embodiments being vaccines comprising an antigen to all five diseases listed.

Particular embodiments are vaccines comprising at least two of the following types of clostridial antigen: *Clostridium perfringens* D toxoid; *Clostridium novyi* B toxoid; *Clostridium chauvoei* anaculture; *Clostridium septicum* toxoid and *Clostridium tetani* toxoid. A particularly preferred embodiment being a vaccine comprising all five antigens listed.

The vaccine may also comprise antigens against other diseases e.g. Pasteurella antigens such as *Pasteurella maltocida* and *Pasteurella haemolyticum;* Corynebacterium antigens such as *Corynebacterium pseudotuberculosis, Corynebacterium renale, Corynebacterium cystitis* and *Corynebacterium pilosum;* and Haemophilus antigens such as *Haemophilus somnus* and *Haemophilus pleuropneumoniae;* Mycoplasma antigens such as *Mycoplasma agalactiae* and *Mycoplasma ovipneumoniae.*

Further preferred embodiments of the invention are those which comprise Corynebacterium antigens such as *Corynebacterium pseudotuberculosis, Corynebacterium renale, Corynebacterium cystitis* and *Corynebacterium pilosum.*

A particularly preferred embodiment of the invention comprises antigens of *Clostridium perfringens* D toxoid; *Clostridium novyi* B toxoid; *Clostridium chauvoei* anaculture; *Clostridium septicum* toxoid, *Clostridium tetani* toxoid and *Corynebacterium pseudotuberculosis.*

The invention particularly relates to vaccines comprising one or more Clostridial antigens in combination with one or more non-Clostridial antigens.

Co-adjuvants may optionally be included in the vaccines of the present invention. The antigens may be in the form of toxoids or cell antigens but if cell antigens are used a co-adjuvant may be required. Such co-adjuvants may suitably include a saponin (e.g. quil A) or cytokines such as Interleukin- 1, 2, and 4 or muramyl dipeptide. Further emulsifiers such as dioctyl decyl ammonium bromide (DDA) may also be included in the vaccines if desired. The vaccine composition of the present invention may contain one or more antigens and one or more emulsifiers and/or one or more co-adjuvants. Supplements such as selenium which is important for growth and reproductive processes may also be included in the vaccine.

Vaccines according to the present invention may be prepared by dissolving antigens in a suitable aqueous medium such as normal saline, stirring the resultant mixture and adding it to a suitable oil phase. The mixture is then stirred (e.g. at 200 to 600 rpm) and/or homogenised (e.g. at 500 to 4500 psi) to the desired viscosity (<200 mPas) and conductivity <0.5 millisiemens at 20° C. Preservatives such as thiomersal may optionally be included in the aqueous mixture prior to adding the antigens. This process is preferably carried out at about 20° C. to about 25° C.

Surprisingly it has been found that the vaccines of the invention can provide a sustained and elevated immune response when administered to the target animals, sheep, in a single dose. They are preferably capable of inducing a response which can be measured, e.g., by ELISA or SN neutralisation titres, for a period of at least 12 months. The vaccine compositions of the present invention are stable and may be stored for several months or even years without loss of antigenic potency. The vaccines are capable of overcoming maternal antibody.

The present invention will now be exemplified with reference to the following Examples by way of illustration only.

EXAMPLE 1

Preparation and Efficacy of a Single Dose Clostridial Plus *Corynebacterium pseudotuberculosis* 6-in-1 Vaccine for Use in Sheep Vaccine compositions were prepared according to Table I below. The compositions were initially prepared by mixing Clostridial and *Corynebacterium pseudotuberculosis* antigens with normal saline and thiomersal at room temperature to prepare the aqueous phase of the vaccines. The pH of the aqueous phase being between pH7 and pH7.5.

For composition 1 the aqueous phase was added to a mixture of Marcol 52 and Montanide 888 (ratio 10.7 to 1 pre-equilibrated to room temperature). This mixture was then homogenised to create a water-in-oil emulsion (viscosity <200 mPas). The dose volume of Composition 1 was 1 mL. Composition 2 was prepared in a similar manner except that an aluminium based adjuvant, Tasgel was added instead of the Marcol 52/Montanide 888 mixture. The aqueous phase/Tasgel mixture was stirred at 100 to 600 rpm at room temperature for 15 minutes and the pH adjusted with HCl to pH 6.5±0.3. The dose volume of Composition 2 was 2 mL.

TABLE I

Vaccine Compositions

| Component | Composition (amount % v/v) | |
|---|---|---|
| | 1 | 2 |
| Cl. perfringens D toxoid | 5.2 | 2.60 |
| Cl. novyi B toxoid | 5.94 | 2.97 |
| Cl. chauvoei anaculture | 4.4 | 2.2 |
| Cl. septicum toxoid | 1.4 | 0.7 |
| Cl. tetani toxoid | 9 | 4.5 |
| C. pseudotuberculosis toxoid | 0.84 | 0.42 |
| MilliQ | 13.9 | 55.6 |
| Thiomersal | | 1 |
| Marcol 52/ISA 888 | 58.5 | |
| Tasgel | | 30 |

The efficacy of the vaccines was tested using a group of thirty approximately four year old pregnant ewes (first cross Border-Leicester) identified by ear tags. The ewes were vaccinated subcutaneously with the vaccines described above approximately two to three weeks prior to the onset of lambing. Twenty lambs born to the previously vaccinated ewes were vaccinated by subcutaneous injection of the vaccine compositions. The vaccine regimes are shown below in Table II:

TABLE II

Vaccine regimes for ewes and lambs

| Group | Vaccine/adjuvant | Lambs or Ewes vaccinated | No. of Animals vaccinated | Dose vol. (mL) |
|---|---|---|---|---|
| 1 | 6 in 1/Tasgel | Ewes | 10 | 2 |
| 2 | 6 in I/M52-M888 | Ewes | 20 | |
| 4 | Non-vaccinate (control) | Lambs | 4 | — |
| 5 | 6 in 1/Tasgel | Lambs | 5 | 2 |
| 6 | Non-vaccinate (control) | Lambs | 11 | — |
| 7 | 6 in 1/M52-M888 | Lambs | 15 | 1 |

Lambs were at least eight weeks old when vaccinated. Only Group 5 received a second vaccination at Week 4, these animals were vaccinated with 6 in 1 vaccine comprising Tasgel as adjuvant. Serum samples were collected from blood centrifuged for 15 minutes at 300rpm and at room temperature. The following assays were performed on serum samples: Cl. perfringens D ELISA was performed on individual serum samples using purified rabbit anti-Cl. perfringens epsilon toxin diluted in carbonate buffer pH9.6 in a 96 well microtitre plate. This was incubated at 37° C. for 2h before purified Cl. perfringens toxin diluted in phosphate buffered saline/Tween 20 (0.1%w/v) was added and the plate incubated at 37° C. for 1 h. Dilutions of sheep sera (and positive and negative sera) were added to the wells and the plate incubated for 1h at 37° C. The plates were then washed with PBS/Tween and a dilution of rabbit anti-sheep IgG horseradish peroxidase conjugate (Biorad) in PBS/Tween added. The plate was incubated at 37° C. for a further hour and then washed with PBS/Tween. Activated substrate (2,2-azino-di-3-ethylbenzthiazolinosulfonate) dissolved in citrate phosphate buffer pH4.6 at 1 mg/mL and activated by addition of 01.3% hydrogen peroxide was added to the plate. Absorbance at 405 nm was read after 30 to 60 minutes using a Titertek Multiscan reader.

The procedure was repeated using purified Cl. tetani toxoid in the Cl. tetani ELISA on individual serum samples.

Mice serum neutralisation titres of pooled group sera for Cl. novyi, Cl. tetani, Cl. septicum and Cl perfringens D were carded out according to the Therapeutic Goods Order No. 30 (Australian Government Publishing Services, 1987).

Corynebacterium pseudotuberculosis (C. pseudotuberculosis) serum neutralisation titres were determined for individuals and pooled sera samples based on observations by Muckel & Giles, Am. J. Vet. Res. 44, 1149–1153, 1983 in order to measure a response to the Corynebacterium pseudotuberculosis. antigens.

The pregnant ewes were monitored on Day 0, Day 1 and Day 14 (Week 2) following vaccination. No ewes appeared distressed. Rectal temperatures were recorded on those days and a summary is shown in Table III.

TABLE III

Rectal temperatures of pregnant ewes prior to and following vaccination

| | Mean rectal temperature (° C.) Day | | |
|---|---|---|---|
| Group vaccine/adjuvant | 0 | 1 | 14 |
| 1 6 in 1/Tasgel | 39.7 ± 0.3 | 40.0 ± 0.5 | 39.6 ± 0.3 |
| 2 6 in 1/M52-M888 | 39.7 ± 0.2 | 40.2 ± 0.5 | 39.5 ± 0.3 |

Site reactions were recorded for the lambs and are shown below in Table IV. They were found to be negligible for each type of vaccination.

TABLE IV

Mean site reactions (cm$^3$) following vaccination of lambs

| Group | Week 4 | Week 8 | Week 12 | Week 20 | Week 26 | Week 30 |
|---|---|---|---|---|---|---|
| 4 | Non vaccinates | 0 (0/3) | | | | |
| 5 | 0 (0/5) | 0 (0/5) | 0 (0/5) | 0 (0/5) | 0 (0/5) | 0 (0/5) |
| 6 | Non vaccinates | 0 (0/6) | | | | |
| 7 | 1.8(1/13) | 0.5(1/15) | 0.6(1/14) | 0(0/15) | 0(0/5) | 0(0/8) |

The figures presented in brackets represent the number of lambs with site reactions/number of lambs per group.

Selected groups were revaccinated at Week 26 and no site reactions were reported at Week 30. The weights of lambs were recorded and are shown below in Table V. No significant difference in weights or weight gain based on 95% confidence interval of the mean for each group at each time point and between non-vaccinates and vaccinates was found ($p>0.05$).

TABLE V

Weights of lambs (kg)

| | Average weight at week | | | | Average weight gain over 12 weeks |
|---|---|---|---|---|---|
| Group | Marking | 4 | 8 | 12 | |
| 4 | 21.6 ± 4.0 | 31.6 ± 4.2 | 35.0 ± 5.0 | 42.3 ± 5.5 | 19.8 ± 2.1 |
| 5 | 22.1 ± 2.5 | 31.1 ± 3.4 | 33.5 ± 3.7 | 38.2 ± 3.9 | 16.1 ± 1.6 |
| 6 | 19.6 ± 5.2 | 27.9 ± 5.3 | 30.8 ± 5.9 | 35.1 ± 6.2 | 15.5 ± 2.5 |
| 7 | 21.3 ± 3.5 | 30.8 ± 3.8 | 32.6 ± 3.9 | 37.4 ± 3.7 | 16.1 ± 3.2 |

Cl. perfringens D ELISA Titres

Cl. perfringens D ELISA titres were determined for both ewes and lambs to evaluate vaccine efficacy. Tables VI and VII record Cl. perfringens D ELISA titres for pregnant ewes and lambs (respectively). Groups 4 and 5 were given a booster vaccination of 6 in 1 vaccine with Tasgel adjuvant at Week 26. Tables VIII and IX show SN's for pregnant ewes and lambs (respectively)

TABLE VI

Cl. perfringens D ELISA (U/mL) of ewes

| Group | adjuvant | Week 0 | Week 17 | Week 37 |
|---|---|---|---|---|
| 1 | 6 in 1 Tasgel 1 × 2 mL dose | 1.4 | 4.3 | 8.7 |
| 2 | 6 in 1 M52-M888 1 × 1 mL dose | 2.6 | 24.4 | 23.2 |

The results displayed are the GMT of individual titres for that group.

TABLE VII

Cl. perfringens D ELISA Titres in lambs

Mean ELISA Titres (U/mL)

| Group | 0 | 4 | 8 | 12 | 20 | 26 | ,,~30 |
|---|---|---|---|---|---|---|---|
| 4 | 1.1 | <1 | <1 | <1 | <1 | <1 | |
| 5 | 2.0 | <1 | <1 | <1 | <1 | <1 | 1.3 |
| 6 | 3.2 | <1 | <1 | <1 | <1 | <1 | |
| 7 | 2.2 | 2.1 | 3.4 | 3.9 | 4.4 | 2.8 | 3.5 |

TABLE VIII

SN Titres in pregnant ewes

| Group | adjuvant | 17 weeks after vaccination | |
|---|---|---|---|
| 1 | 6 in 1 Tasgel 1 × 2 mL dose | Cl. perf D | 5.5–11 |
| | | Cl. tet | 8–10 |
| | | Cl. novyi B | 6–8 |
| | | Cl. sept | <2 |
| 2 | 6 in 1 M52-M888 1 × 1 mL dose | Cl. perf D | 13.2–16.5 |
| | | Cl. tet | >12 |
| | | Cl. novyi B | 3–5 |
| | | Cl. sept | >10 |

TABLE IX

SN Results for lambs

| Group | Vaccine | Week 0 | | Week 8 | |
|---|---|---|---|---|---|
| 5 | 6 in 1 Tasgel 2 × 2 mL dose | Cl. perf D | 1.7–2.5 | Cl. perf D | <3.65 |
| | | Cl. tet | 2.5–3.8 | Cl. tet | <2 |
| | | Cl. novyi B | 2.3–3.5 | Cl. novyi B | 1.5–2.3 |
| | | Cl. sept | <2 | Cl. sept | <2 |
| | | C. pseudot | 2.1 | C. pseudot | 0.2 |
| 7 | 6 in 1 M52-M888 1 × 1 mL dose | Cl. perf D | <1.1 | Cl. perf D | <3.6 |
| | | Cl. tet | 1.7–2.5 | Cl. tet | 2.5–3.8 |
| | | Cl. novyi B | 1.5–2.3 | Cl. novyi B | 2.3–3.5 |
| | | Cl. sept | <2 | Cl. sept | <2 |
| | | C. pseudot | 1.2 | C. pseudot | 0.1 |

| Group | Vaccine | Week 26 | | Week 30 | |
|---|---|---|---|---|---|
| 5 | 6 in 1 Tasgel 2 × 2 mL dose | Cl. perf D | <1.1 | Cl. perf D | <4 |
| | | Cl. tet | <1.1 | Cl. tet | >4.1 |
| | | Cl. novyi B | <1.0 | Cl. novyi B | 7.1–10.7 |
| | | Cl. sept | <2.0 | Cl. sept | <2.0 |
| | | C. pseudot | 0.8 | | |
| 7 | 6 in 1 M52-M888 1 × 1 mL dose | Cl. perf D | 1.1–1.7 | | |
| | | Cl. tet | <1.1 | | |
| | | Cl. novyi B | <1.0 | | |
| | | Cl. sept | <2.0 | | |
| | | C. pseudot | 1.1 | | |

Vaccination of lambs in Group 7 with the single dose M52-M888 adjuvanted vaccine (the same vaccines as their mothers were vaccinated with) indicated that maternal antibody could be overcome by providing a response to vaccination, when compared to the standard (Group 5). Comparing non-vaccinates with vaccinates (Groups 4 and 5 or groups 6 and 7) maternal antibody appeared to decline to a level below the sensitivity of the ELISA by Week 4 following marking. The 95% confidence intervals of the mean for each group indicate that from Week 8 onwards only Group 7 has a statistically significantly higher titre than all other groups (p<0.05). Thus, based on these ELISA results and similar analysis for other Clostridial and bacterial components, the capacity of a single dose of the M52-M888 adjuvanted vaccine to generate responses is at least as good as the two dose vaccine. Furthermore the M52-M888 adjuvanted vaccine was administered in a single dose.

EXAMPLE 2

Preparation and Efficacy of a Single Dose Clostridial 5-in1 Vaccine for Use in Sheep Vaccine compositions used in this example were prepared in a similar manner to the compositions described above in Example 1 (see Table I) except that the C. pseudotuberculosis antigen was omitted. Selenium (1 mg per dose) was added to the aqueous phase prior to mixing with either Marcol 52/Montanide 888 or Tasgel.

Fine wool Merryville Merino ewes and lambs, identified by numbered ear tags, were vaccinated subcutaneously in the left side of the neck in accordance with the regime set out below in Table X. They were vaccinated on the right side of the neck when a second and/or booster dose was required. All these lambs were derived from Merino ewes that had been previously vaccinated with 5 in 1 Tasgel vaccine 1 month prior to lambing.

TABLE X

Vaccine groups

| Group | Vaccine Antigen/Adjuvant | No. of Lambs | Dose volume (mL) |
|---|---|---|---|
| 1 | Non-vaccinates | 10 | — |
| 2 | 5 in 1/Tasgel | 18 | 2 |
| 3 | 5 in 1 + Se/Tasgel | 18 | 2 |
| 4 | 5 in 1/M52-M888 | 18 | 1 |
| 5 | 5 in 1 Se/M52-M888 | 18 | 1 |

Lambs were vaccinated when four to eight weeks old. Groups 2 and 3 were vaccinated with a second dose of 5 in 1 Tasgel vaccine at week 4. Groups 2,3,4 and 5 received a booster vaccination with the respective vaccinates for the group at week 51.

Serum samples were collected from blood centrifuged at 300 rpm, 15 min at room temperature. The assays described above in Example 1 were performed on the serum samples.

Site reactions following vaccination were not found in any of the Merino lambs. No adverse affects on the lambs' general well being as a result of vaccination were observed.

Cl. perfringens D and Cl. tetani ELISA Titres

The response of the lambs to vaccination was assessed by measurement of Cl. perfringens D and Cl. tetani antibody responses using specific ELISAs. Cl. Perfringens D results are presented below in Table XI and Cl. tetani results are presented in Table XII.

TABLE XI

*Cl. pedringens* D ELISA Titre in Lambs (U/mL)

| | | Vaccination | Cl. perfringens ELISA Titre (U/mL) WEEK | | | | | | | |
|---|---|---|---|---|---|---|---|---|---|---|
| Group | Vaccine Antigens/Adjuvant | (week) | 0 | 4 | 8 | 12 | 19 | 26 | 51 | 55 |
| 1 | Non-vaccinate | | 1.6 | <1 | <1 | <1 | <1 | <1 | <1 | <1 |
| 2 | 5 in 1 Tasgel | 0, 4 | 2.2 | <1 | <1 | 2.9 | <1 | <1 | <1 | 1.4 |
| 3 | 5 in 1 + Se/Tasgel | 0, 4 | 3.6 | <1 | <1 | 1 | <1 | <1 | <1 | 2.4 |
| 4 | 5 in 1 M52/M888 | 0 | 2.7 | 5.1 | 11.5 | 17 | 80 | 13.6 | 12.6 | 15.6 |
| 5 | 5 in 1 + SeM52/M888 | 0 | <1 | 1.3 | 4.8 | 9.2 | 20 | 10 | 8 | 16.8 |

TABLE XII

*Cl. tetani* ELISA Titre in Lambs (U/mL)

| | | Vaccination | Cl. tetani ELISA Titre (U/mL) WEEK | | | | | | | |
|---|---|---|---|---|---|---|---|---|---|---|
| Group | Vaccine Antigens/Adjuvant | (week) | 0 | 4 | 8 | 12 | 19 | 26 | 51 | 55 |
| 1 | Non-vaccinate | | 1.9 | <1 | <1 | <1 | <1 | <1 | <1 | <1 |
| 2 | 5 in 1 Tasgel | 0, 4 | <1 | <1 | <1 | <1 | <1 | <1 | <1 | 1.9 |
| 3 | 5 in 1 + Se/Tasgel | 0, 4 | <1 | <1 | <1 | <1 | <1 | <1 | <1 | 1.6 |
| 4 | 5 in 1/M52-M888 | 0 | <1 | <1 | 4.5 | 10.4 | 2.3 | 3.4 | 1.3 | 10.4 |
| 5 | 5 in 1 + Se/M52-M888 | 0 | 1.4 | <1 | 5.2 | 5.6 | 1 | 2.4 | 1.5 | 10.4 |

Both *Cl. perfringens* D and *Cl. tetani* ELISA titres in lambs were detected over 51 weeks following a single dose vaccination with the M52-M888 adjuvanted vaccine formulation. In comparison, ELISA titres were not-detectable following two doses of the 5 in 1 gel vaccine. This may be due to the levels of maternal antibody present in the lambs. In Group 4 where maternal antibody was detected at marking (week 0), the M52-M888 adjuvanted vaccine formulation overcame maternal antibody to produce a strong response.

The M52-M888 adjuvanted vaccines showed higher efficacy than the 5 in 1 Tasgel adjuvanted vaccine formulations, Furthermore the M52-M888 adjuvanted vaccine formulation (Group 4) was used in a single dose regime compared to a two dose regime for the gel formulations (Groups 2 and 3). The addition of selenium did not offer any immunological advantage, although it is known to act as an immune stimulant. It is primarily added as a mineral supplement to these vaccines.

SN Titres in Lambs

SN titres for *Cl. perfringens* D, *Cl. tetani*, *Cl. septicum* and *Cl. novyi* B were determined for selected pooled group sera samples from Groups 1 to 5. At Week 12, only lambs vaccinated with the 5 in 1 M52/M888 adjuvanted vaccine formulation (Group 4) gave detectable SN titres for the components *Cl. perfringens* D, *Cl. tetani*, *Cl. septicum* and *Cl. novyi* B. By Week 19 SN titres for *Cl. tetani* and *Cl. novyi* B remained detectable for this formulation. Results are presented below in Table )XIII. Pooled group sera from lambs vaccinated with formulations containing selenium were only assayed at Week 12 for *Cl. perfringens* D and *Cl. tetani*. Results were similar to that found in lambs vaccinated with formulations without selenium.

TABLE XIII

Serum neutralisation titres in lambs

| Group | Vaccine (Antigen/Adjuvant) | Vaccination (week) | Antigen | Week 0 | Week 4 | Week 8 | Week 12 | Week 19 | Week 51 | Week 55 |
|---|---|---|---|---|---|---|---|---|---|---|
| 1 | Non-vaccinates | | Cl. perfringens D | <3.6 | | | <1.4 | <3.0 | <1.1 | |
| | | | Cl. tetani | <2.0 | | | <2.2 | <2.2 | <1.2 | |
| | | | Cl. septicum | NA | NT | NT | NT | <1.8 | <2 | NT |
| | | | Cl novyi B | <1.5 | | | NT | <1.4 | <1 | |
| 2 | 5 in 1 Tasgel | 0, 4 | Cl. perfringens D | <3.6 | <3.6 | <3.6 | <1.4 | <3.0 | <1.1 | <1.1 |
| | | | Cl. tetani | <2.0 | <2.0 | <2.0 | <2.2 | <2.2 | <1.2 | NA |
| | | | Cl. septicum | <2.2 | <2.2 | <1.80 | <1.8 | <1.8 | <2 | <2 |
| | | | Cl novyi B | 1.5–2.3 | <1.5 | 2.3–3.5 | <1.6 | <1.4 | <1 | 3.5–5.3 |
| 3 | 5 in 1 + Se Tasgel | 0, 4 | Cl. perfringens D | | | | <1.4 | | | |
| | | | Cl. tetani | | | | <2.2 | | | |
| | | | Cl. septicum | NT | NT | NT | NT | NT | NT | NT |
| | | | Cl novyi B | | | | NT | | | |
| 4 | 5 in 1 M52–M888 | 0 | Cl. perfringens D | <3.6 | 3.6–4.5 | 9.0–13.6 | 4.6–6.9 | <3.0 | <1.1 | >8.8 |
| | | | Cl. tetani | <2.0 | 2.5–3.8 | 8.6 | 6.2–9.3 | 4.1–6.2 | <1.2 | 1.8–2.8 |
| | | | Cl. septicum | <2.2 | <2.2 | 2.3–3.4 | 2.3–3.4 | <1.8 | <2 | 8.6–12.9 |
| | | | Cl novyi B | <1.5 | 3.5–5.3 | 8.0–12.0 | 5.3–7.9 | 2.1–3.2 | <1 | >8 |

TABLE XIII-continued

Serum neutralisation titres in lambs

| Group | Vaccine (Antigen/Adjuvant) | Vaccination (week) | Antigen | Week 0 | Week 4 | Week 8 | Week 12 | Week 19 | Week 51 | Week 55 |
|---|---|---|---|---|---|---|---|---|---|---|
| 5 | 5 in 1 + Se M52–M888 | 0 | Cl. perfringens D | | | | 3 | | | |
| | | | Cl. tetani | | | | 2.8–4.1 | | | |
| | | | Cl. septicum | NT | NT | NT | NT | NT | NT | NT |
| | | | Cl novyi B | | | | NT | | | |

Rabbit Potency

The vaccines were assessed in the standard rabbit potency test (Therapeutic Goods Order No. 30 Australian Government Publishing 1987). A summary of results is presented in Table XIV. The vaccine formulation of 5 in 1 M52-M888 adjuvanted vaccine formulation (Group 4) passed potency in all fractions, following a single dose vaccination. This result was similar to that of the standard gel vaccine following two doses (Group 2). The vaccines with selenium (Groups 3 and 5) were not assessed in the rabbit potency test.

TABLE XIV

Initial Rabbit Potency of Vaccines

| | | SN U/mL | | | |
|---|---|---|---|---|---|
| Group | Vaccine Antigens/ Adjuvant | Cl. tetani | Cl. perfringens D | Cl. septicum | Cl. novyi B |
| 2 | 5 in 1/ Tasgel | 2.8–4.1 | 9–13.5 | 5.6–8.4 | 4.7–7.1 |
| 4 CODEX PASS | 5 in 1/ M52-M888 | 9.3–13.9 2.5 | 20.2–30.4 5 | 3.8–5.6 2.5 | >10.7 3.5 |

Rabbit Potency Shelf Life

The 5 in 1 M52-M888 adjuvanted vaccine formulation (Group 4) was assessed for stability at 2, 14 and 22 months post manufacture in the rabbit potency test. Results are presented below in Table XV. They passed potency in all fractions.

TABLE XV

Rabbit Potency Shelf Life

| | | SN (U/mi | | | |
|---|---|---|---|---|---|
| Vaccine Antigens/ Adjuvant | Shelf Life at Test (Months) | Cl. tetani | Cl. perfringens D | Cl. septicum | Cl. novyi B |
| 5 in 1 Tasgel | 2 | 2.8–4.1 | 9–13.5 | 5.6–8.4 | 9.7–7.1 |
| | 14 | 2.5–3.8 | 6–9 | 7.6–11.4 | 3.5–5.3 |
| 5 in 1 M52-M888 CODEX PASS | 2 | 9.3–13.9 | 20.2–30.3 | 3.8–5.6 | >10.7 |
| | 14 | 11.2 | 18.7–20.1 | >11.6 | >12 |
| | 22 | >12.9 | >28 | 9.514.2 | >12 |
| | | 2.5 | 5 | 2.5 | 3.5 |

Guinea Pig Cl. chauvoei Challenge

The Cl. chauvoei guinea pig challenge test is a regulatory requirement (Therapeutic Goods Act, 1966, Therapeutic Goods Order No. 30). Vaccines with a Cl. chauvoei fraction must pass this test in order to be released for use. A pass in the challenge test is at present defined as: "10 out of 10 guinea pigs vaccinated with two doses (4 weeks apart) of an aluminium hydroxide adjuvanted clostridial vaccine, surviving a Cl. chauvoei challenge at 2 weeks post second vaccination for 5 days post challenge". This result is compared with non-vaccinated controls which must succumb to challenge within 3 days. The vaccines were assessed in the Cl. chauvoei guinea-pig challenge test and the results of the challenge tests are shown below in Table XVI.

TABLE XVI

Guinea Pig Cl. chauvoei Challenge

| Group | Vaccine/Adjuvant | Survivors/No. Challenged | Pass/Fail (Challenge) |
|---|---|---|---|
| 4 CODEX PASS | 5 in 1 M52-M888 | 5/5, 10/10 10/10 | Pass |

The results discussed above indicate that single dose vaccine is more efficacious and provides a sustained immune response to the clostridial antigens as determined by ELISA and SN tests. The single dose vaccine is safe, with negligible site reactions and passed the rabbit potency test in all fractions (Cl. perfringens D, Cl. tetani, Cl. septicum, Cl. novyi B and Cl. chauvoei). and the guinea pig Cl chauvoei challenge test.

What is claimed is:

1. A sheep vaccine water-in-oil emulsion composition, which is storage-stable as said water-in-oil emulsion composition, said emulsion composition comprising:
   a) an oily adjuvant acceptable for veterinary purposes consisting essentially of:
      i) about 50% to about 70% by weight of said emulsion of a white mineral oil having a molecular weight of about 250 to 300 and
      ii) about 2% to about 10% by volume of said emulsion of a mannitol oleate emulsifier, and
   b) an aqueous phase comprising at least two clostridial vaccine antigens.

2. A vaccine composition as claimed in claim 1 wherein the vaccine composition has a viscosity of about 100 milliPascals to about 200 millipascals.

3. A vaccine composition as claimed in claim 1 wherein the mannitol oleate emulsifier is an anhydromannitol ether octadecanoate.

4. A vaccine composition as claimed in claim 1 wherein the vaccine composition comprises two or more of the following Clostridial antigens: Clostridium perfringens type A, B, C and D, Clostridium septicum, Clostridium tetani, Clostridium chauvoei, Clostridium novyi type B, Clostridium sordelli, and Clostridium haemolyticum.

5. A vaccine composition as claimed in claim 1 wherein the vaccine composition comprises clostridial antigens which are obtained from strains that cause one or more of the following: Lamb dysentery, Pulpy Kidney disease (enterotoxaemia), Malignant Oedema (blood poisoning), Tetanus, Blackleg disease and Black disease.

6. A vaccine composition as claimed in claim 1 wherein the vaccine composition further comprises antigens against a non-clostridial disease.

7. A vaccine composition as claimed in claim 6 wherein the vaccine comprises Corynebacterium antigens.

8. The vaccine composition as claimed in claim 1 wherein said clostridial antigens are selected from the group consisting of *Clostridium perfringens* type A, B, C and D, *Clostridium septicum, Clostridium tetani, Clostridium chauvoei, Clostridium novyi* type B, *Clostridium sordelli, Clostridium haemolyticum,* and *Clostridium botulinum* C and D.

9. The vaccine composition as claimed in claim 8 wherein said composition comprises five clostridial vaccine antigens.

10. The vaccine composition as claimed in claim 9 wherein said clostridial antigens are selected from the group consisting of perfringens type A, B, C and D, *Clostridium septicum, Clostridium tetani, Clostridium chauvoei*, and *Clostridium novyi* type B.

11. The vaccine composition as claimed in claim 10 wherein said clostridial antigens are *Clostridium perfringens* D toxoid, *Clostridium septicum* toxoid, *Clostridium tetani* toxoid, *Clostridium chauvoei* anaculture, and *Clostridium novyi* type B toxoid.

12. The vaccine composition as claimed in 11 wherein said white mineral oil is present in said emulsion in an amount of about 53% to about 63% by weight thereof, and said mannitol oleate emulsifier is present in said emulsion in an amount of about 3% to about 7% by volume thereof.

13. The vaccine composition as claimed in claim 10, further comprising at least one antigen against a non-clostridial disease selected from the group consisting of *Corynebacterium pseudotuberculosis, Corynebacterium renale, Corynebacterium cystitis* and *Corynebacterium pilosum.*

14. The vaccine composition as claimed in claim 13 wherein said non-clostridial antigen is *Corynebacterium pseudotuberculosis.*

15. The vaccine composition as claimed in claim 1 wherein said composition is a stirred or homogenized composition.

* * * * *

UNITED STATES PATENT AND TRADEMARK OFFICE
CERTIFICATE OF CORRECTION

PATENT NO. : 6,524,592 B2  Page 1 of 1
DATED : February 25, 2003
INVENTOR(S) : Richard Buchta, Christopher Schwartzkoff and Philip Ralph Lehrbach It is certified that error appears in the above-identified patent and that said Letters Patent is hereby corrected as shown below:

<u>Title page,</u>
Item [30], Foreign Application Priority Data, should read as follows:
-- October 17, 1997 (GB).......... 9722035.4 --

Signed and Sealed this

Nineteenth Day of August, 2003

JAMES E. ROGAN
*Director of the United States Patent and Trademark Office*